United States Patent [19]

Lambert

[11] Patent Number: 4,706,694

[45] Date of Patent: Nov. 17, 1987

[54] DENTAL FLOSS DEVICE

[76] Inventor: Joseph Lambert, 410 Dogwood La., Christiansburg, Va. 24073

[21] Appl. No.: 843,341

[22] Filed: Mar. 24, 1986

[51] Int. Cl.⁴ .............................................. A61C 15/00
[52] U.S. Cl. .............................. 132/92 R; 132/92 A; 132/91
[58] Field of Search ...................... 132/92 R, 92 A, 91; 433/130

[56] References Cited

U.S. PATENT DOCUMENTS

| | | | |
|---|---|---|---|
| 1,003,785 | 9/1911 | Paschall | 132/92 A |
| 1,306,998 | 6/1919 | Dimitroff | 132/92 A |
| 1,990,404 | 2/1935 | Doner | 132/92 R |
| 2,033,662 | 3/1936 | Witt | 433/130 |
| 2,354,454 | 7/1944 | Geffner | 132/91 |
| 2,837,098 | 6/1958 | Sorboro | 132/92 R |
| 3,106,216 | 10/1963 | Kirby | 132/92 R |
| 3,908,678 | 9/1975 | Conn et al. | 132/92 A |
| 4,005,721 | 2/1977 | Yasumoto | 132/91 |
| 4,151,851 | 5/1979 | Bragg | 132/91 |

FOREIGN PATENT DOCUMENTS 735125 11/1932 France ................................. 132/91

Primary Examiner—John J. Wilson
Attorney, Agent, or Firm—Reed Smith Shaw & McClay

[57] ABSTRACT

The disclosure relates to a device for supporting floss and maintaining that floss with sufficient tension for use in connection with the gums and cavities in the oral cavity of the user. The device includes a handle and a carrier secured for rotatable relationship with the handle to facilitate use of the device within the oral cavity. On the carrier there is arranged a spool for carrying a supply of floss and reel for receiving the end of the floss remote from spool. Two prongs extend from the carrier to expose a portion of the floss under tension for use in the oral cavity. A knife is positioned adjacent the reel for cutting spent floss extending beyond the reel.

5 Claims, 6 Drawing Figures

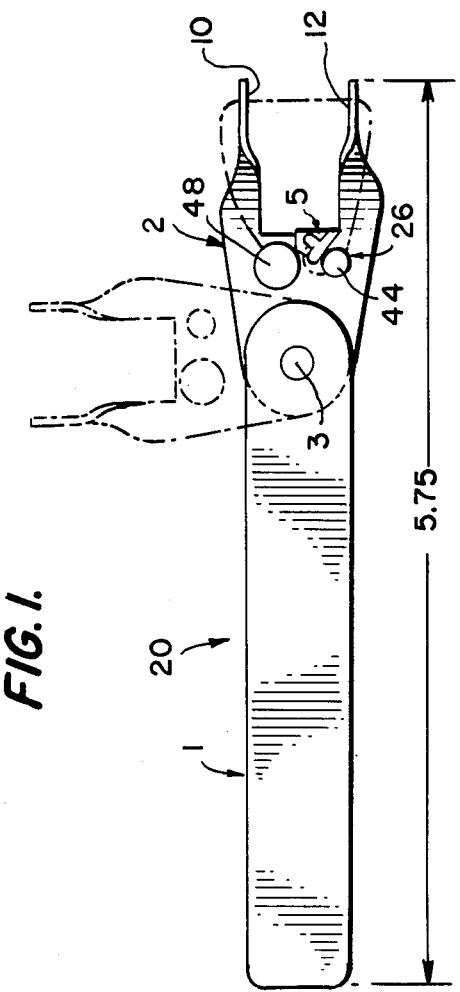
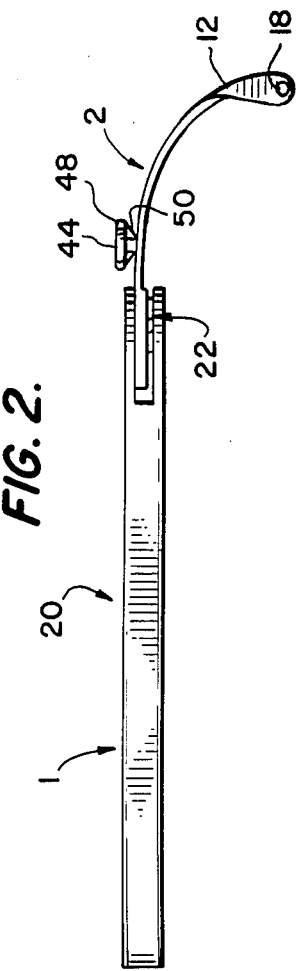
FIG. 1.
FIG. 2.

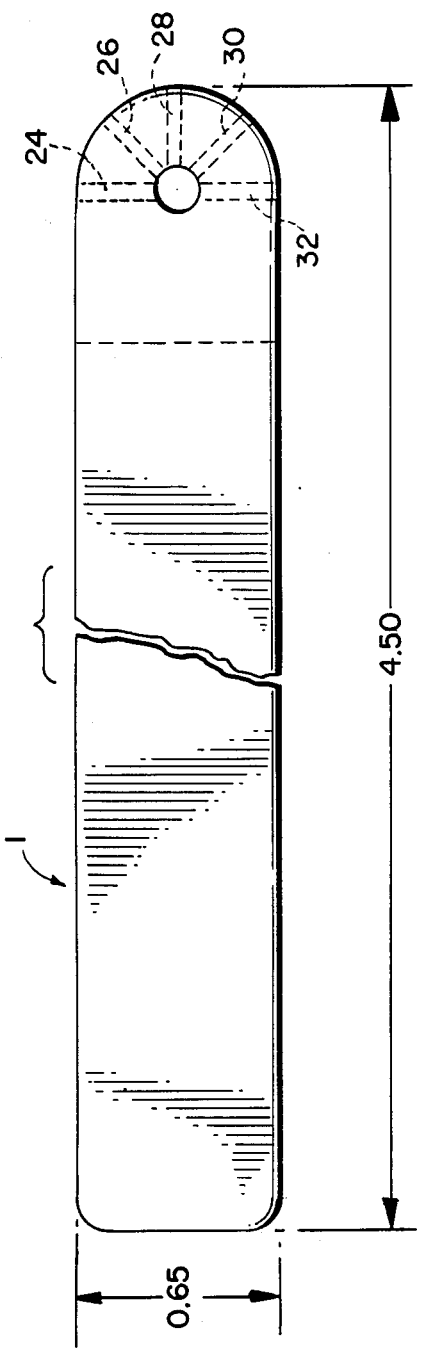
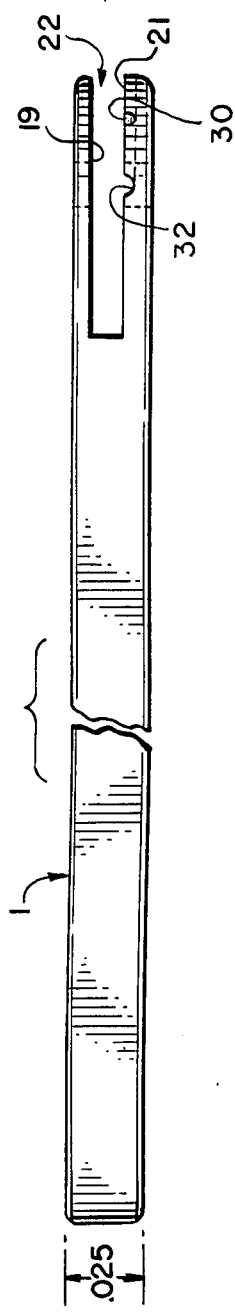

DENTAL FLOSS DEVICE

BACKGROUND AND DISCUSSION OF THE INVENTION

Tooth flossing has become an important mode of maintaining the health of one's gums and teeth. One mode of flossing is accomplished by simply tearing a portion of floss from a dispenser and wrapping the floss about the fingers of two hands for insertion into the oral cavity. This approach is frought with problems. It can be an uncomfortable exercise since the floss can be tightened about the fingers to the extent that it actually becomes painful. Furthermore, it can be difficult to gain access to certain portions of the oral cavity because of the size and position of the fingers about which the floss is wrapped.

Devices have been developed to permit flossing without the need to employ the fingers as the carrier for the floss. Such devices have taken many forms none of which proved entirely satisfactory. Some earlier dental floss holders were forked shaped and provided prongs on which the floss could be secured. The fork could be moved relative to the handle and fixed in a desired location. For this purpose a thumb screw was provided to engage complementary apertures to secure the fork in the selected position. Such a device did not carry a spool for continually furnishing a source of floss material. Consequently, the user was required to keep a separate source of material and draw from that separate source each time the exposed floss on the device required replacement.

Other devices which did provide spools were extremely complicated, bulky, and consequently, are expensive to manufacture and difficult to use. An example of such a device has outwardly projecting arms on a supporting frame with the arms spaced from each other a distance to receive teeth therebetween. Guide members carried by the outer ends of the arms receive and permit relative movement of the dental floss as it passes from a supply reel to a take-up reel. Forward and rearward angular movement is imparted alternatively to the reels. The forward angular movment is greater than the rearward angular movement whereby the dental floss is reciprocated back and forth between the armsand moves progressively forward to the take-up reel.

To accomplish this interaction a number of moving parts are required. The supply reel and take-up reel are arranged in a housing above the actuating mechanism and the motor with its power supply. Such a system is inordinately complicated, expensive, bulky, and depends on the quality of the power supply for proper operation.

Applicant's invention overcomes many of the problems associated with flossing devices which have existed heretofore. It is relatively simple in design while accomplishing many of the needs of the user perferably with only moving part. It is adjustable to permit access to otherwise difficult to reach portions of the oral cavity. A relatively small but sufficient supply spool is provided to achieve for the device a relatively slim profile. The floss carrier includes a mechanism to prevent the floss from becoming disengaged from the device during use. The head of the device which carries the floss is movable between a number of positions to permit the most comfortable configuration for the user. Furthermore, the prong configuration is one which limits exposure of the floss to sharp edges which could sever the floss during use. A cut-off knife is provided adjacent a take-up reel where spent floss can be cut and discarded.

The above has been a discussion of some of the problems associated with the prior art and features of the invention which overcome these problems. Other advantages of the invention will be apparent from the detailed discussion of the invention which will follow.

BRIEF DESCRIPTION OF THE DRAWINGS

FIG. 1 is a plan view of the device.

FIG. 2 is an elevated view of the device as shown in FIG. 1.

FIG. 3 is an enlarged view of a handle portion of the device as shown in FIG. 1.

FIG. 4 is an elevated view of the handle shown in FIG. 3.

DETAILED DESCRIPTION OF THE PREFERRED EMBODIMENT

Figure 5:
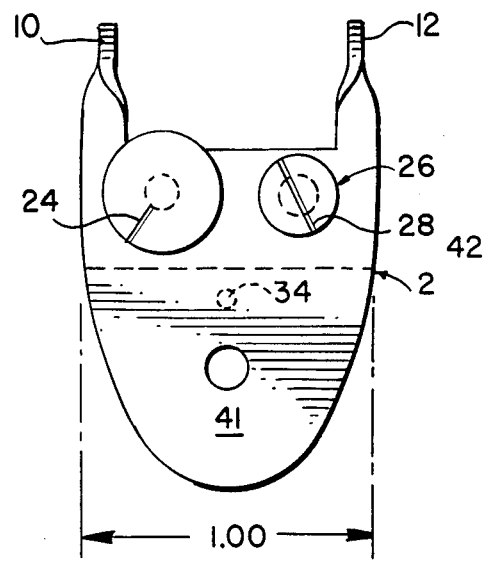
FIG. 5 is an enlarged view of the head portion of the device as shown in FIG. 1.

As can be seen in FIG. 1, the flossing device 20 includes a handle 1 and a head 2 which pivots relative handle 1 about rivet 3 defining the axis of rotation. Head 2 is configured to form two prongs 10 and 12 having apertures 16 and 18 in spaced relationship and to define a path perpendicular to the axis of rotation through which the floss passes and is held for use on the gums and teeth of the oral cavity. A detent mechanism is provided to maintain the head 2 at one of five positions relative to the handle 1.

As can be seen in FIG. 2, the handle has a relatively flat configuration and defines a slot 22 in which the head 2 moves among the five positions. The detent mechanism is achieved by the interaction portion of the head and the handle within the slot 22. The slot 22, formed in one end of handle 1 as shown, has upper and lower opposed internal faces 19 and 21. In lower face 21 there are formed five equally spaced grooves 24, 26, 28, 30, and 32. Each of these grooves extends radially from the axis of rotation for head 2 to the outer periphery of the handle. Head 2 includes pivot portion 41 and floss carrier 42. Pivot portion 41 has a thickness less than the width of slot 22 to permit rotation therein. This pivot portion 41 defines an upper face 40 and a lower face 38, the latter of which defines a ball socket 34 for carrying ball 36. When in place within the slot 22 ball 36 can engage each groove to hold the head 2 in place until moved by the user. The head 2 is sufficiently flexible to deform when it is desired to rotate head 22 to a new position, permitting the ball to move out of a groove and forcing the ball 36 into the next groove when registered during rotation. With this mechanism the head will be detented at each groove engaged by ball 36 and held in that position until overcome by the user.

Figure 6:
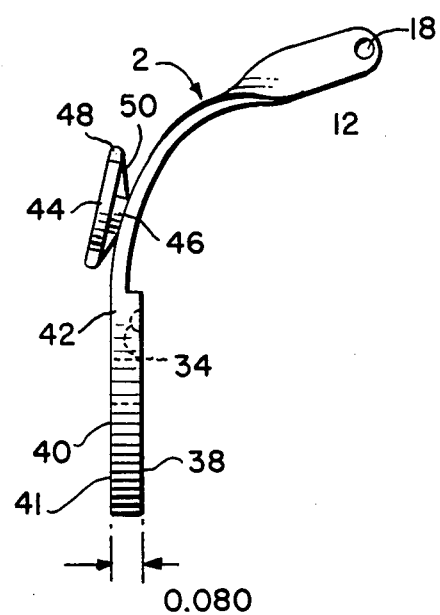
FIG. 6 is an elevated view of head as shown in FIG. 5.

The head 2 is configured to hold, dispense and expose floss for flossing action by the user. As can be seen from FIGS. 1 and 2, head 2 is rather flat in configuration bent down out of the plane of the handle 1. Two prongs 18, 20 extend from carrier 42 in spaced relationship in a plane displaced from that of handle 1. In this embodiment these prongs are formed by bending the prongs through an arc as can be seen in FIG. 6 and twisted such that apertures 18 and 20 are colinear in a path parallel to the plane of the handle 1. Each prong is twisted to the extent that the end of the prongs define a plane perpindicular to that of handle 1. Other configurations of handle 1, head 2, etc. can be used to achieve the desired location and operation of the elements described above.

Upper surface of carrier 42 supports a feed 22 and take-up reel 26. These elements cooperate with prongs 10 and 12, apertures 18 and 20 to hold and dispense the floss. As can best be seen in FIGS. 5 and 6, feed 22 is in the form of a spool secured to upper surface of carrier 42 adjacent prong 10 as an inverted cone. The size of this particular spool permits at least three yards of floss to be wrapped about the spool's conical surface 50. Top 48 of feed 22 contains a pinch slot 24 to hold the floss in place and prevent it from becoming unraveled during use. Displaced from feed 22 is take-up reel 26 located colinearly with feed 22 along a line parallel to that of the aperture 18 and 22 and adjacent to prong 12. Reel 26 has a caphead 44 and shaft 46. The shaft 46 is secured to the carrier 42 and has a diameter less than that of caphead 44 to provide an area for supporting a portion of floss having passed through aperture 18. The top of reel 26 defines a pinch slot 28 for holding a portion of floss in place after having been wrapped around shaft 46. With this configuration the floss is presented with relatively smooth surfaces in the path through the apertures and between the reel 28 and feed 22.

In operation three yards of floss is initially fixed in pinch slot 24 and wrapped about conical surface 50 of feed 22. A portion of the floss is then passed sequentially along outer surface of surface of prong 12 to reel 26 where it is wrapped about shaft 46 one or more turns with a sufficient portion of the floss remaining to be fixed in pinch slot 28. In wrapping the floss about the reel it can be drawn to sufficiently tight to suit the user. Any excess floss is removed by cutting floss at cut-off 5 located on the carrier adjacent the reel 28. Head 2 is then rotated to a position which is most comfortable to the user for reaching certain parts of the oral cavity.

As a portion of the floss becomes worn, that portion of the floss in pinch slot 28 is removed therefrom to slaken the tension sufficiently and permit unwinding a newer section of floss from feed 22. The newer section is then threaded through the apertures as described before and secured to the reel with the desired tension.

As shown the handle 2 is about 4.5 inches in length, 0.025 inches in thickness and 0.65 inches in width and planar in configuration. The head has a thickness of 0.08 inches or less and a maximum width of about one inch. The feed 22 and reel 28 have a height of no more than 0.1 inches. The overall length of the device is about 5.75 inches.

In the preferred embodiment described herein, the various elements are made of metal. However, they can be formed from plastic or other materials which meet the requirements of operations, function and result consistent with the full scope of invention to which the invention is entitle. In this regard the claims which follow define the scope of the invention along with the equivalents to which the invention is entitled.

What is claimed is:

1. A device for holding floss comprising: A handle; a carrier secured to said handle for relative movement therewith; said carrier defining two spaced prongs each with an aperture therethrough where floss can pass and be exposed for use by the user; said prongs extending into a plane displaced from that of the handle; said carrier having a spool for supporting a source of floss and a reel for receiving an end of the floss remote from said source; said reel having a pinch slot for fixing said end of said floss thereto and cooperating with said spool and said prongs to provide a means for maintaining tension on the floss extending through the apertures; a knife fixed to said carrier adjacent said reel for cutting spent floss; said spool being located adjacent one of said prongs and said reel being located adjacent the other of said prongs; said carrier being movable among at least two positions on said handle; a detent means for maintaining said carrier in any one of said positions as selected until moved therefrom by the user.

2. The device for holding floss according to claim 1 wherein said detent means includes grooves in said handle corresponding to each of said positions and a ball carried by said carrier for releasable engagement with each of said grooves.

3. The device for holding floss according to claim 2 wherein each of said spaced prongs has an end portion defining said aperture therethrough, each of said prongs being twisted to a plane perpendicular to the plane defined by said carrier to provide a smooth surface between the apertures, the spool for supporting a source of floss and the reel for receiving an end of the floss.

4. A device for holding floss comprising: a handle; a head portion, including a floss carrier defining two spaced prongs, each prong with an aperture therethrough where floss can pass and be exposed for use by the user; said carrier having an upper surface and a lower surface, said upper surface having a spool for supporting a floss exposed to the user, a reel for receiving an end of the floss remote from said source, said spool being adjacent one prong and said reel being adjacent another prong on the upper surface of said carrier; said reel having a pinch slot for fixing said end of said floss thereto and cooperating with said spool and said prongs to provide a means for maintaining tension on the floss extending through the apertures; a knife affixed to said carrier adjacent said reel for cutting spent floss; said carrier being movable among a number of positions on said handle; a detent means for maintaining said carrier in any one of said positions as selected until moved therefrom by the user; said prongs being twisted into a position perpendicular to the plane of said carrier.

5. A device for holding floss comprising: A handle; a carrier secured to said handle for relative movement therewith; said carrier defining two space prongs each with an aperture therethrough where floss can pass and be exposed for use by the user; said prongs extending into a place displaced from that of the handle; said carrier having a spool for supporting a source of floss and a reel for receiving an end of the floss remote from said source; said reel having a pinch slot for fixing said end of said floss thereto and cooperating with said spool and said prongs to provide a means for maintaining tension on the floss extending through the apertures; a knife fixed to said carrier adjacent said reel for cutting spent floss; said spool being located adjacent one of said prongs and said reel being located adjacent the other of said prongs; and said carrier being movable among five positions on said handle; a detent means for maintaining said carrier in any one of said positions as selected until moved therefrom by the user; and said detent means including grooves in said handle corresponding to each of said positions and a ball carried by said carrier for releasable engagement with each of said grooves.

* * * * *